United States Patent
Ellering

(10) Patent No.: US 8,523,761 B2
(45) Date of Patent: *Sep. 3, 2013

(54) PENILE PROSTHETIC RESERVOIR

(75) Inventor: Nicholas Ellering, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/437,009

(22) Filed: Apr. 2, 2012

(65) Prior Publication Data

US 2013/0053633 A1    Feb. 28, 2013

Related U.S. Application Data

(63) Continuation of application No. 13/217,277, filed on Aug. 25, 2011.

(30) Foreign Application Priority Data

Aug. 24, 2011   (DK) .................................. 2011 70464

(51) Int. Cl.
*A61F 5/00*        (2006.01)
(52) U.S. Cl.
USPC .......................................................... 600/40
(58) Field of Classification Search
USPC ............................... 600/37–41; 128/897–898
See application file for complete search history.

(56) References Cited

U.S. PATENT DOCUMENTS

| | | | |
|---|---|---|---|
| 4,559,931 | A  | 12/1985 | Fischell |
| 4,881,530 | A  | 11/1989 | Trick |
| 7,946,975 | B2 | 5/2011  | George et al. |
| 2006/0235267 | A1 | 10/2006 | George et al. |
| 2009/0209808 | A1 | 8/2009  | Abdelmalek |
| 2009/0253953 | A1 | 10/2009 | Morningstar |
| 2011/0201880 | A1 | 8/2011  | Fogarty |

OTHER PUBLICATIONS

DK Patent Application PA 2012 70545—Office Action dated Oct. 9, 2012.

*Primary Examiner* — John Lacyk
(74) *Attorney, Agent, or Firm* — Coloplast Corp., Coloplast A/S; Nick Baumann

(57) ABSTRACT

An implantable penile prosthetic includes a pump attachable between a reservoir and a cylinder that is implantable into a corpora cavernosum of a penis. The reservoir has a central longitudinal axis and includes a wall connected between a first edge of a first surface and a second edge of a second surface. The first surface is concave relative to the first edge and the second surface is concave relative to the second edge such that each of the first and second surfaces form a depression in the reservoir when the reservoir is empty of liquid. The reservoir expands to contain liquid such that the first surface and the second surface are both convex relative to the central longitudinal axis.

20 Claims, 7 Drawing Sheets

PENILE PROSTHETIC RESERVOIR

BACKGROUND

An implanted penile prosthetic is effective in relieving erectile dysfunction in men.

A penile prosthetic typically includes a cylinder that is implanted in each corpora cavernosum of the penis, a reservoir implanted in the abdomen that communicates with the cylinders, and a pump, often located in the scrotum, that is employed to move liquid from the reservoir into the cylinders.

In a typical application, the user squeezes a bulb of the pump multiple times to incrementally draw liquid out of the reservoir, into the bulb, and eventually into the cylinders. The repeated squeezing of the bulb moves the liquid from the reservoir into the cylinders, which incrementally deflates the reservoir and incrementally inflates the cylinders to eventually provide the user with an erect penis. The user may return the penis to its flaccid state by selectively transferring the liquid from the cylinders back into the reservoir.

The above-described penile prosthetics have proven effective in relieving erectile dysfunction in men. However, there is a continued desire for more efficient, discreet, and effective penile prostheses.

SUMMARY

One aspect provides an implantable penile prosthetic including a pump attachable between a reservoir and a cylinder that is implantable into a corpora cavernosum of a penis. The reservoir has a central longitudinal axis and includes a wall connected between a first edge of a first surface and a second edge of a second surface. The first surface is concave relative to the first edge and the second surface is concave relative to the second edge such that each of the first and second surfaces form a depression in the reservoir when the reservoir is empty of liquid. The reservoir expands to contain liquid such that the first surface and the second surface are both convex relative to the central longitudinal axis.

One aspect provides a method of implanting a penile prosthetic in a man. The method includes providing a reservoir having a first major surface separated from to a second major surface by a side wall, the first major surface and the second major surface are both concave and form opposed depressions in the reservoir when the reservoir is empty of liquid. The method additionally includes connecting the reservoir to a pump that is connected to a cylinder, implanting the pump in the scrotum, implanting the cylinder in a corpora cavernosum of the penis, and implanting the reservoir in the man.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 5 is a cross-sectional view of the pump in a configuration suited to pressurize the pressure reservoir illustrated in FIG. 1.

DETAILED DESCRIPTION

Figure 1:
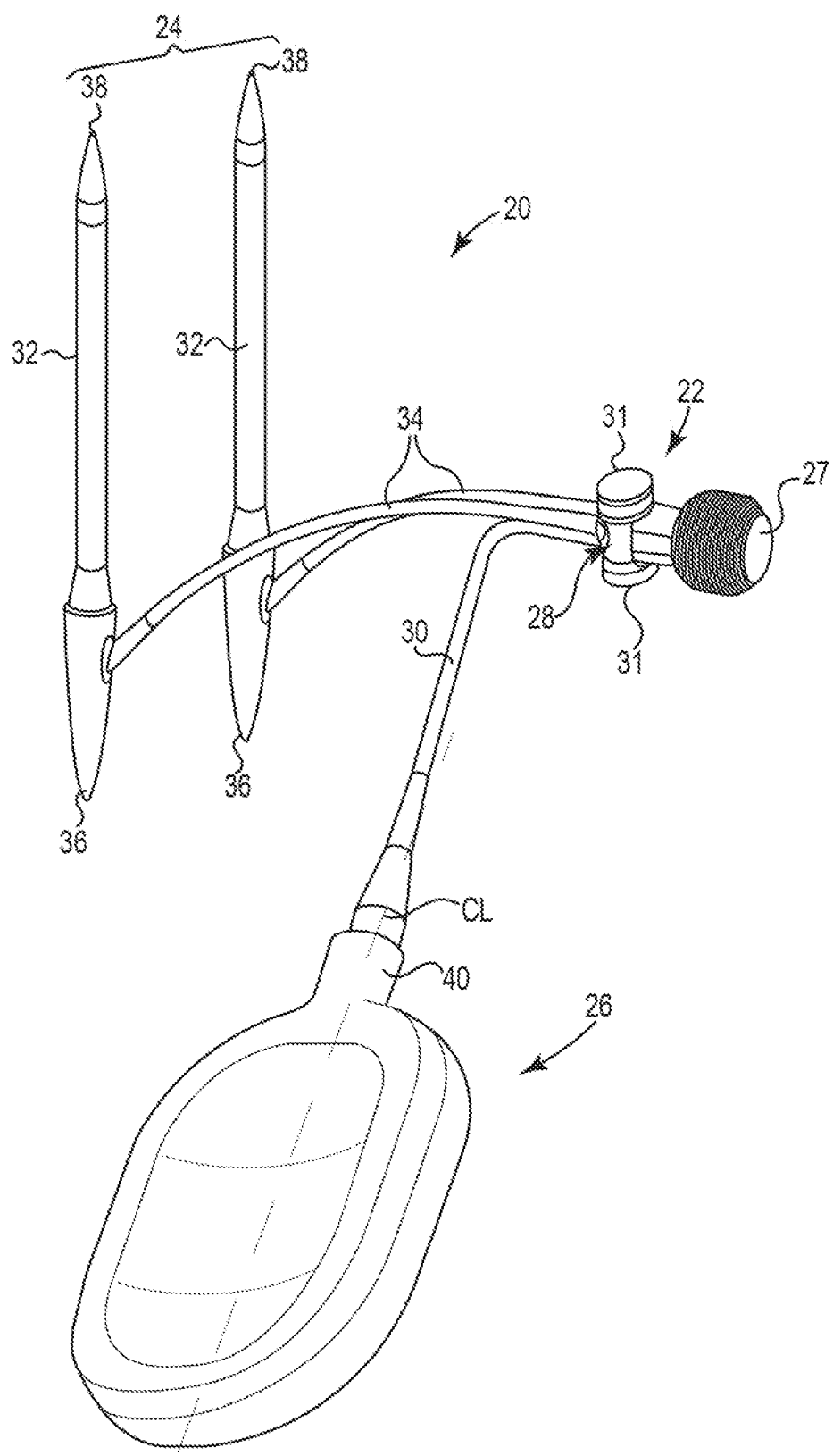
FIG. 1 is a perspective view of one embodiment of an implantable penile prosthetic including a reservoir.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

"Liquid" means a substance having molecules that do not disperse such that the liquid resists compression and the molecules of the liquid will not disperse to fill all spaces of a container in which the liquid is disposed. Saline is an example of a liquid.

In this specification, a "major surface" is a surface of a three-dimensional object that provides the object with most of its surface area. As an example, a sheet of paper generally has a front side and a back side with a thin edge thickness between the front and back sides; the front side and the back side are both major surfaces.

In this specification, a reservoir is "filled with liquid" when the reservoir contains some amount of liquid; that is, the reservoir is not empty of liquid. In this specification, a "reservoir expands to contain liquid" means that the reservoir flexes to contain some amount of liquid more than the reservoir contains in its empty state.

Embodiments provide an implantable penile prosthetic having a reservoir that is provided with a low profile that is unobtrusive to the user. The reservoir includes opposing concave depressions formed in the major surfaces that configure the reservoir with a low profile when implanted. The opposing concave depressions of the reservoir allow the reservoir to expand comfortably and discreetly when implanted and filled with liquid. When implanted, the reservoir presents such a discreet profile as to be nearly imperceptible. Embodiments of the reservoir include differential concave surfaces that expand to different extents, which allows the reservoir to expand more inwardly into the body than outwardly, and this contributes to its discreet implanted profile.

FIG. 1 is a perspective view of one embodiment of an implantable penile prosthetic 20. The penile prosthetic 20 includes a pump 22 attachable to a penile implant 24 and a reservoir 26. Generally, suitable connections are made as the pump 22 is implanted into the scrotum of the user, the penile implant 24 is implanted into corpora cavernosa of the penis, and the reservoir 26 is implanted within the abdomen of the user. The penile prosthetic 20 is illustrated in a configuration in which the components have been coupled together and the reservoir 26 is not filled with liquid.

The pump 22 includes a bulb 27 that is operable (for example by squeezing of the bulb 27) to move liquid stored in the reservoir 26 into the penile implant 24. In one embodiment, the penile prosthetic 20 includes a release mechanism 28 associated with the pump 22 that is operable to hold or "check" the liquid in the penile implant 24 after the liquid has been transferred into the penile implant 24. The release mechanism 28 is configured to be manually operated by the user to selectively release the liquid in the penile implant 24 back to the reservoir 26 through the tube 30, for example when pads 31 on the release mechanism 28 are pushed. The pump 22 is fabricated from material suitable for body implantation, such as silicone, polymers such as urethanes, blends of polymers with urethane, copolymers of urethane, or the like.

The penile implant 24 includes a pair of inflatable cylinders 32, each of which is sized to be implanted into a corpora cavernosum of the penis. Each of the cylinders 32 is connected to the pump 22 by a tube 34. Each of the cylinders 32 includes a proximal end 36 opposite a distal end 38. During implantation, the proximal end 36 (also called a rear tip) is implanted toward the crus of the penis and the distal end 38 is implanted within the glans penis. The cylinders 32 are fabricated from material configured to collapse and be flexible when the cylinders 32 are deflated to provide the penis with a flaccid state and expand when the cylinders 32 are inflated with liquid to provide the penis with an erect state. Suitable material for fabricating the cylinders 32 includes silicone, polymers such as urethanes, blends of polymers with urethane, copolymers of urethane, or the like. Suitable cylinders are available from Coloplast Corp., Minneapolis, Minn.

The reservoir 26 includes a neck 40 that is attached to the tube 30. The reservoir includes a central longitudinal axis CL that projects through a center of the neck 40. The "top" and "bottom" surfaces are major surfaces, and each of the major surfaces of the reservoir 26 is concave when the reservoir 26 is empty of liquid (as it is first implanted prior to being filled with liquid), which provides the reservoir 26 with a low profile. In one embodiment, each of the major concave surfaces is uniformly concave (the major surfaces are equally concave or "bi-concave"). The concave configuration of the major surfaces of the reservoir 26 allows the reservoir 26 to expand a substantial amount when filled with liquid (when the cylinders 32 are flaccid). In one embodiment, the concave major surfaces expand to convex shapes when the reservoir 26 is filled with liquid, which translates the reservoir 26 into a nearly cylindrical shape. In one embodiment, the major concave surfaces are not uniformly concave.

Figure 2:
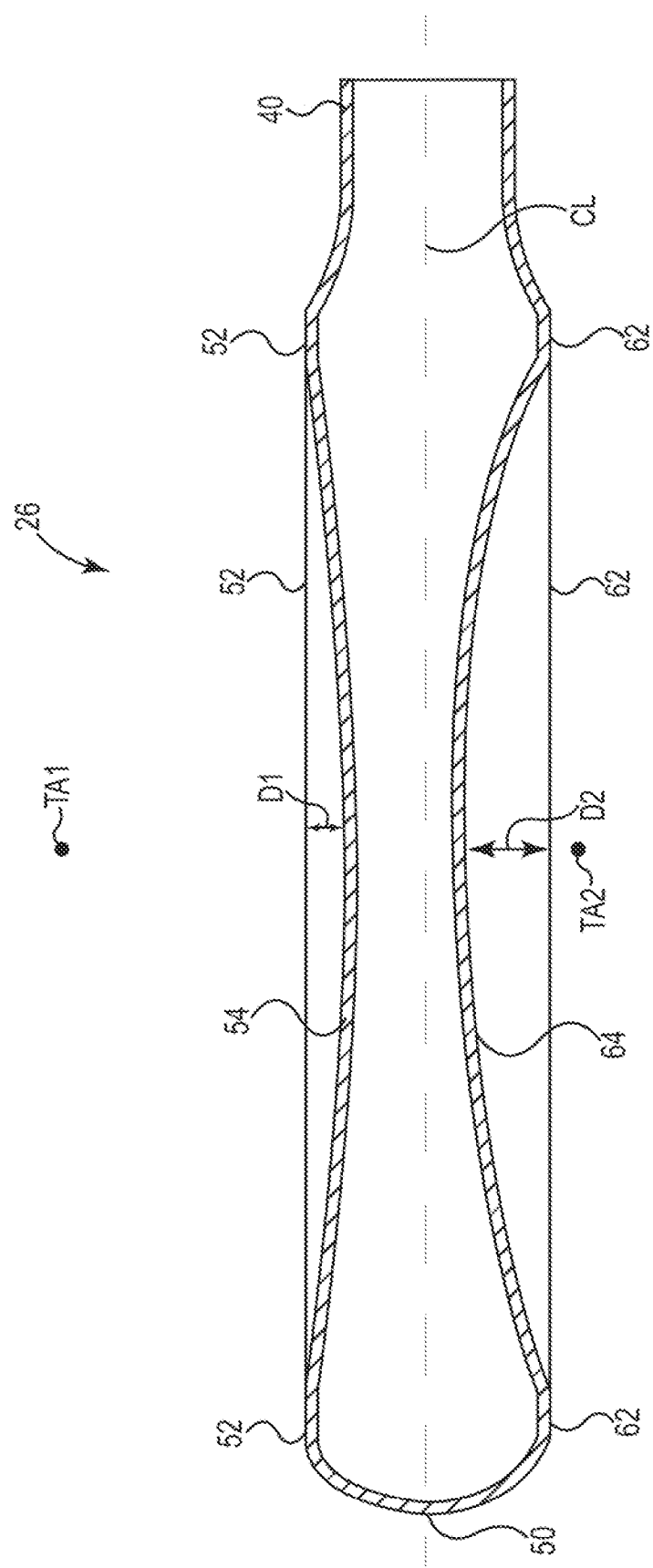
FIG. 2 is a side cross-sectional view of the reservoir illustrated in FIG. 1.

FIG. 2 is a side cross-sectional view of the reservoir 26. The reservoir 26 includes an end wall 50 opposite the neck 40. The end wall 50 extends between a first edge 52 of a first surface 54 and a second edge 62 of a second surface 64. In one embodiment, the first surface 54 is concave relative to the first edge 52 and the second surface 64 is concave relative to the second edge 62 such that each of the first and second surfaces 54, 64 form a depression in the reservoir 26 when the reservoir is empty of liquid (as illustrated). In one embodiment, the first edge 52 and the second edge 62 are substantially planar when the reservoir 26 is empty of liquid and the first surface 54 is concave relative to the planar first edge 52 and the second surface 64 is concave relative to the planar second edge 62.

In one embodiment, the first surface 54 is equally concave with the second surface 64 ("bi-concave") and the depth of the first surface 54 relative to the first edge 52 is substantially equal to the depth of the second surface 64 relative the second edge 62.

In one embodiment, the concavity of the first surface 54 is different from the concavity of the second surface 64. In an exemplary embodiment, the first surface 54 has a depth D1 and the second surface 64 has a depth D2, where the depth D2 is greater than the depth D1. In one embodiment, a radius of curvature for the first surface 54 is less than a radius of curvature for the second surface 64 such that the reservoir 26 has major surfaces 54, 64 that have different concavity.

In one embodiment, the first edge 52 and the first surface 54 combine to form a first major surface, and the second edge 62 and the second surface 64 combine to form a second major surface, where the major surfaces are distinguished over the other surfaces (the end wall 50 and the neck 40, for example) in that they each have more area than other surfaces of the reservoir 26.

The side view of FIG. 2 illustrates that the first surface 54 has a curvature that extends between the end wall 50 and the neck 40, where the first surface 54 curves about a first transverse axis TA1 that is not parallel to the central longitudinal axis CL. In a similar manner, the second surface 64 has a curvature that extends between the end wall 50 and the neck 40 that curves about a second transverse axis TA2 that is not parallel to the central longitudinal axis CL.

In one embodiment, the reservoir 26 is fabricated around a mold such that the thickness of the end wall 50, the thickness of the neck 40, and the thickness of the surfaces 54, 64 are substantially equal. The first surface 54 and the second surface 64 are configured to be flexible. With this in mind, one embodiment of the reservoir 26 provides for the thickness of the first and second major surfaces 54, 64 to be thinner than the neck 40 and the end wall 50. Suitable material for fabricating the reservoir 26 includes silicone, polymers such as urethanes, blends of polymers with urethane, copolymers of urethane, or the like. In one exemplary fabrication process, one of the suitable materials identified above is coated over a mandrel, and when hardened, is peeled off of the mandrel to provide the reservoir 26 with the concave first and second major surfaces 54, 64.

Figure 3:
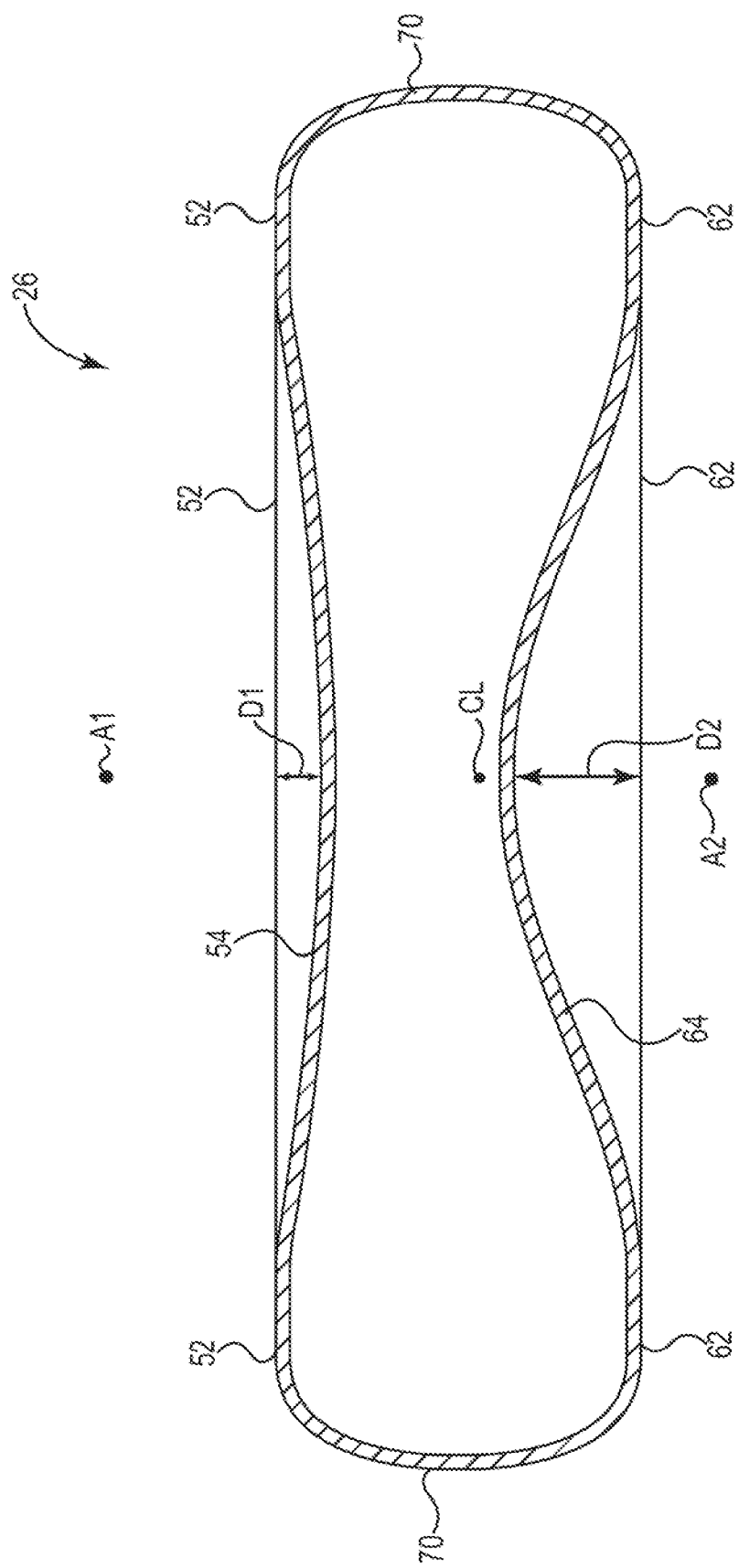
FIG. 3 is an end cross-sectional view of the reservoir illustrated in FIG. 1.

FIG. 3 is an end cross-sectional view of the reservoir 26. The reservoir 26 includes sidewalls 70 that extend between the first and second major surfaces 54, 64. In one embodiment, the sidewalls 70 are generally straight sidewalls that are parallel with the central longitudinal axis CL. In one embodiment, the sidewalls 70 generally curve between the first edge 52 and the second edge 62.

In one embodiment, the first surface 54 is concave and curves about a first longitudinal axis A1 that is parallel with the central longitudinal axis CL, and the second surface 64 is concave and curves about a second longitudinal axis A2 that is parallel to both the central longitudinal axis CL and the first longitudinal axis A1.

In one embodiment, the first surface 54 is a top surface and the second surface 62 is a bottom surface, and the top and bottom surfaces 54, 64 each generally curve about a different axis that is parallel to the central longitudinal axis CL.

In one embodiment, both of the first and second major surfaces 54, 64 are concave and extend between the sidewalls 70 (i.e., laterally) at a first radius of curvature and extend between the neck 40 and the end wall 50 (i.e., longitudinally as in FIG. 2) with a concavity having a second radius of curvature. That is to say, each of the first and second major surfaces 54, 64 have a complex concave curvature.

Figure 4:
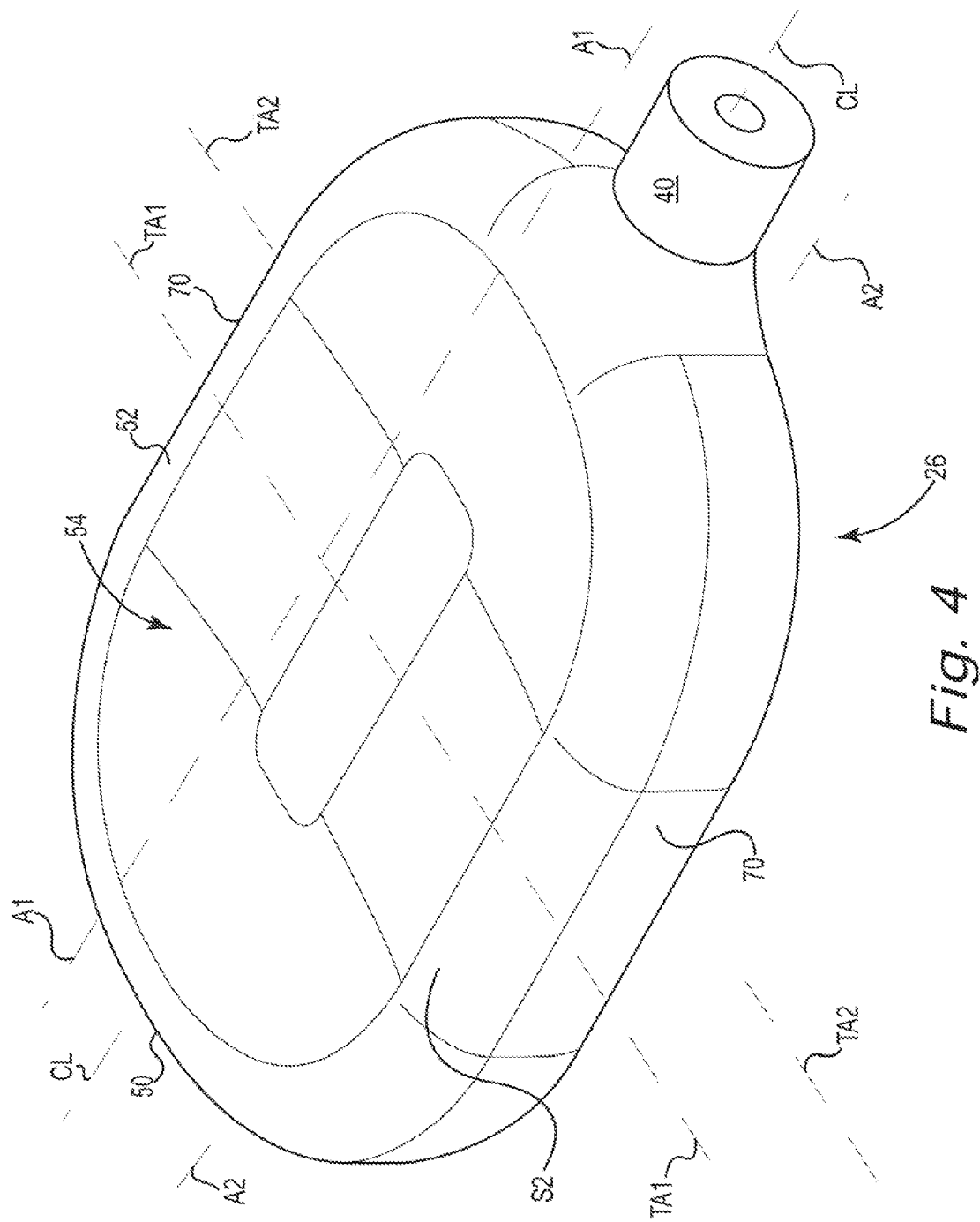
FIG. 4 is a top perspective view of the reservoir illustrated in FIG. 1.
Figure 5:
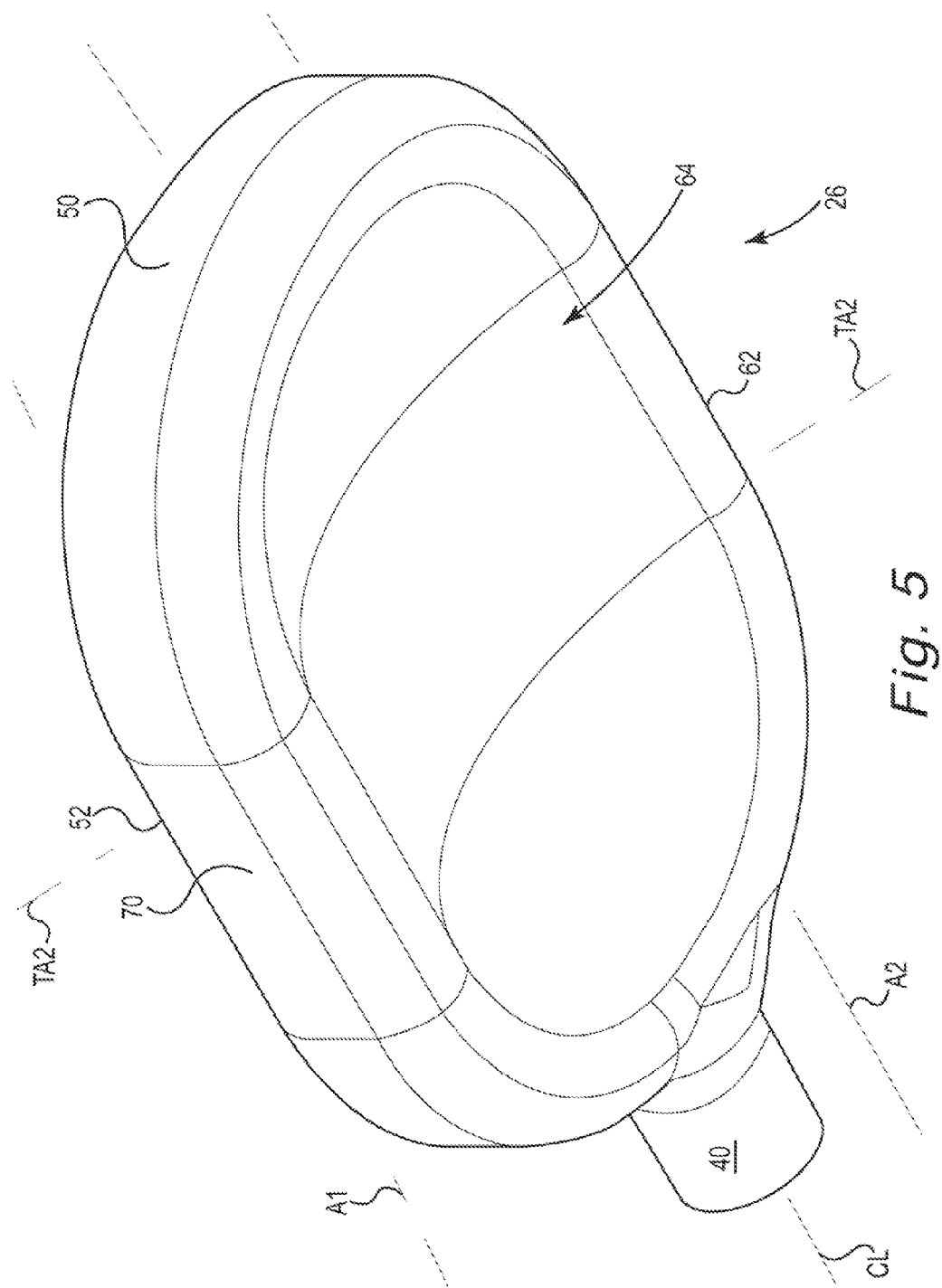
FIG. 5 is a bottom perspective view of the reservoir illustrated in FIG. 1.

FIG. 4 and FIG. 5 are prospective views of the reservoir 26 empty of liquid and in a configuration as provided to a surgical facility prior to implantation of the reservoir 26.

FIG. 4 is a top perspective view of the reservoir 26 illustrating the complex concave curvature of the first surface 54. The various axes are illustrated to orient the reader; the central longitudinal axis CL extends through a point in an opening of the neck 40, the first longitudinal axis A1 is imposed above the reservoir 26 in a longitudinal direction, the second longitudinal axis A2 is imposed below the reservoir 26 in a longitudinal direction, the first transverse axis TA1 is imposed above the reservoir 26 in a transverse direction, and the second transverse axis TA2 is imposed below the reservoir 26 in a transverse direction. In one embodiment, when the reservoir 26 is empty, the central longitudinal axis CL extends through a center of the opening of the neck 40.

The first surface 54 includes a first curvature extending between the end wall 50 and the neck 40 that curves about the first transverse axis TA1 and a second curvature extending between the sidewalls 70 that curves about the first longitudinal axis A1. In one embodiment, the complex curvature of the first surface 54 is contained within the first edge 52 when the reservoir 26 is empty of liquid. The first edge 52 provides a flat surface extending around the perimeter of the reservoir 26. The sidewalls 70 and the first and second edges 52, 62 smoothly blend into the neck 40.

FIG. 5 is a bottom perspective view of the reservoir 26 illustrating the complex concave curvature of the second surface 64. The second surface 64 includes a first curvature extending between the end wall 50 and the neck 40 that curves about the second transverse axis TA2 and a second curvature extending between the sidewalls 70 that curves about the second longitudinal axis A2.

Each of the first surface 54 and a second surface 64 has a concave curvature when the reservoir 26 is empty of liquid. Embodiments provide the reservoir 26 with substantially equal concave curvature on each of the first surface 54 and the second surface 64. In one embodiment, the depth of the curvature of the second surface 64 is deeper than the depth of the curvature of the first surface 54 (FIG. 4) as illustrated in FIG. 2.

In one embodiment, the first surface 54 is a top surface, and the second surface 64 is a bottom surface that is spaced apart from the top surface 54 by a distance equal to a height of the side wall 70, and the top and bottom surfaces 54, 64 each generally curve about a different axis A1, A2, respectively, that is parallel to the central longitudinal axis CL.

Figure 6:
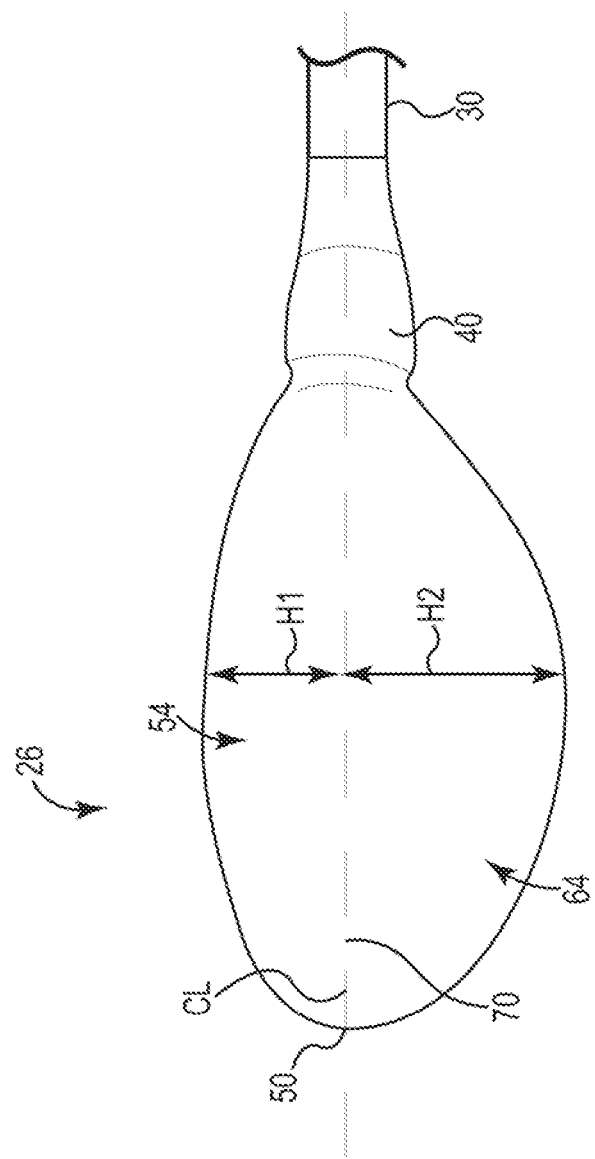
FIG. 6 is a side view of the reservoir illustrated in FIG. 1 when filled with liquid.

FIG. 6 is a side view of the reservoir 26 connected to the pump 22 by the tube 30 and filled with liquid. When the reservoir 26 is filled with liquid, the reservoir expands away from the central longitudinal axis CL. The first surface 54 expands away from the central longitudinal axis CL by the distance H1 and a second surface 64 expands away from the central longitudinal axis by the distance H2. In one embodiment, the distance H1 is substantially equal to the distance H2. In one embodiment, the distance H1 is less than the distance H2 and the reservoir 26 expands with a first surface expansion that is different from the second surface expansion. For example, in one embodiment the first surface expansion is less than the second surface expansion to allow the reservoir 26 to preferentially expand more in one direction (inward into the patient) than another direction (outward from the patient). That is, when the reservoir 26 expands, the first surface is less convex than the second surface is convex, relative to the central longitudinal axis.

Figure 7:
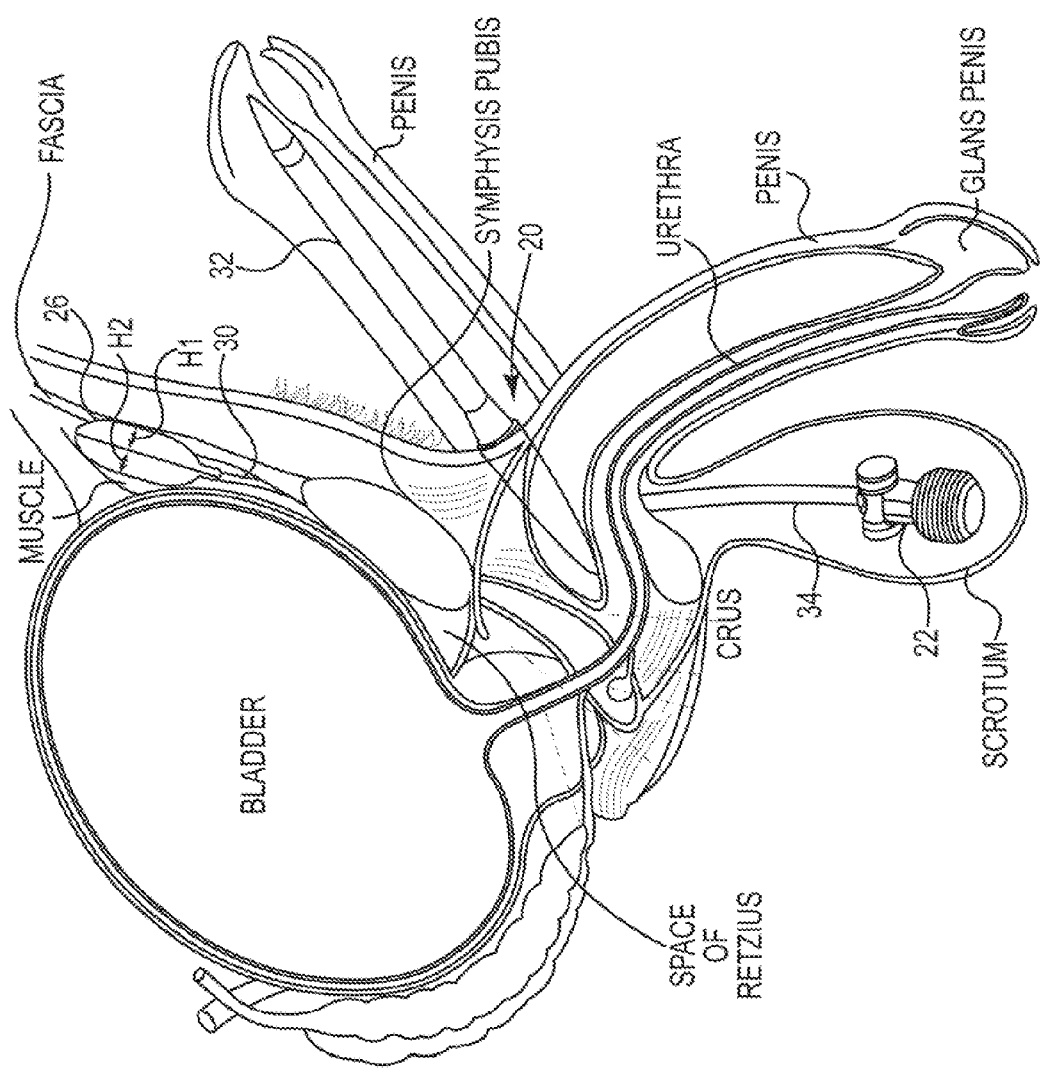
FIG. 7 is a schematic view of the implantable penile prosthetic illustrated in FIG. 1 implanted in a man.

FIG. 7 is a schematic view of the penile prosthetic 20 implanted in a man. The pump 22 is implanted in the scrotum, each of the cylinders 32 is implanted into one of the corpora cavernosa, and the reservoir 26 is implanted within the patient. The pump 22 is connected to the reservoir 26 by the tube 30, and the pump 22 is connected to the cylinders 32 by the tubes 34. After implantation of the prosthetic 20, the surgeon will evaluate function by filling the reservoir 26 with an amount of liquid, for example between 50-350 mL. Thereafter, the function of the prosthetic 20 is evaluated for inflation and deflation of the cylinders 32 and for an absence of leaking from the reservoir connections. The surgeon confirms acceptable performance of the prosthetic 20 prior to closing the surgical site.

In one embodiment, the reservoir 26 is implanted in the space of Retzius behind the symphysis pubis. Thus, one acceptable location for implantation of the reservoir 26 is behind the pubic bone.

In one embodiment, the reservoir 26 is implanted in the abdomen between muscle and fascia. For example, in one embodiment the reservoir 26 is implanted in front of the puborectalis muscle and behind the transversalis fascia. The concave curvature of the first and second surfaces 54, 64 provides the reservoir 26 with a compact (or flat) profile configured for discreet implantation into the wall of the abdomen.

In one embodiment, the reservoir 26 is implanted subcutaneously anterior the fascia, one example of which is anterior to the transversalis fascia.

In one embodiment, the reservoir 26 is implanted subcutaneously anterior to the abdominal muscle, one example of which is anterior to the puborectalis muscle.

In one embodiment, the reservoir 26 is configured to provide differential expansion such that one of the major surfaces 54, 64 expands outward from the central longitudinal axis CL to a greater extent than the other major surface. As illustrated in FIG. 7, the second major surface 64 (FIG. 6) is configured to expand more than the first major surface 54, and the second major surface 64 is oriented to face posterior the patient such that the first major surface is oriented to face anterior the patient. When the reservoir 26 expands, the second major surface 64 expands inward into the user to reduce perception of the implanted reservoir, thus allowing the implanted reservoir 26 to be discreet even if implanted near the surface of the skin.

Embodiments provide a reservoir having opposing concave depressions formed in the major surfaces that configure the reservoir with a low profile when implanted. The opposing concave depressions of the reservoir allow the reservoir to expand comfortably and discreetly when implanted and filled with liquid. Embodiments of the reservoir include differential concave surfaces that expand different amounts that configure the reservoir to expand more inwardly into the body than outwardly, for example, and this contributes to its discreet implanted profile.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An implantable penile prosthetic comprising:
a pump attachable between a reservoir and a cylinder that is implantable into a corpora cavernosum of a penis, the reservoir having a central longitudinal axis and comprising:
a wall connected between a first edge of a first surface and a second edge of a second surface, the first surface concave relative to the first edge and the second surface concave relative to the second edge such that each of the first and second surfaces form a depression in the reservoir when the reservoir is empty of liquid; and
wherein the reservoir expands to contain liquid such that the first surface and the second surface are both convex relative to the central longitudinal axis;
wherein a depth of the concave first surface is less than a depth of the concave second surface such that the reservoir has different concavity for the first surface and the second surface.

2. A body implantable penile prosthetic reservoir comprising:
a first major surface opposed to a second major surface, the first major surface and the second major surface both concave and forming opposed depressions in the reservoir when the reservoir is empty of liquid;
wherein a radius of curvature for the first major surface is less than a radius of curvature for the second major surface such that the reservoir has major surfaces with different concavity that configures the reservoir for more inward expansion into the user than outward expansion when implanted.

3. The reservoir of claim 2, further comprising:
a wall connected between a first edge of the first major surface and a second edge of the second major surface;
wherein a height of the wall is configured such that the first major surface is separated from the second major surface by less than one inch.

4. The reservoir of claim 2, further comprising:
a wall connected between a first edge of the first major surface and a second edge of the second major surface, with the first major surface concave relative to the first edge and the second major surface concave relative to the second edge.

5. The reservoir of claim 2, wherein the reservoir has major surfaces with different concavity when the reservoir is empty of liquid and the reservoir has major surfaces with different convexity when the reservoir is filled with liquid.

6. The implantable penile prosthetic of claim 1, wherein the first edge of the first surface and the second edge of the second surface are both substantially planar when the reservoir is empty of liquid.

7. The implantable penile prosthetic of claim 1, wherein the reservoir is configured to expand with a first surface expansion that is different from a second surface expansion.

8. The implantable penile prosthetic of claim 7, wherein when the reservoir expands, the first surface expansion is less than the second surface expansion and the first surface is less convex than the second surface is convex, relative to the central longitudinal axis.

9. The implantable penile prosthetic of claim 8, wherein, relative to a user, the first surface is an outward facing surface and the second surface is an inward facing surface, such that when the reservoir is implanted and the reservoir expands to contain liquid, a majority of expansion for the reservoir is inward into the user to reduce perception of the implanted reservoir.

10. The implantable penile prosthetic of claim 1, wherein the first surface is concave and curves about a first longitudinal axis parallel to the central longitudinal axis and the second surface is concave and curves about a second longitudinal axis that is parallel to both the central longitudinal axis and the first longitudinal axis.

11. The implantable penile prosthetic of claim 1, wherein the wall comprises side walls that are generally parallel with the central longitudinal axis, an end wall connected to the side walls, and a neck defining an opening into the reservoir.

12. The implantable penile prosthetic of claim 11, wherein the first surface is concave and has a curvature between the end wall and the neck that curves about a first transverse axis that is not parallel to the central longitudinal axis and the second surface is concave and has a curvature between the end wall and the neck that curves about a second transverse axis that is not parallel to the central longitudinal axis.

13. The implantable penile prosthetic of claim 11, wherein the first surface is a top surface, and the second surface is a bottom surface that is spaced apart from the top surface by a distance equal to a height of the side wall, and the top and bottom surfaces each generally curve about a different axis that is parallel to the central longitudinal axis.

14. The implantable penile prosthetic of claim 13, wherein the height of the side wall is configured such that the top surface is separated from the bottom surface by less than one inch.

15. The implantable penile prosthetic of claim 13, wherein the central longitudinal axis extends through a center of the neck.

16. An implantable penile prosthetic comprising:
a pump attachable between a reservoir and a cylinder that is implantable into a corpora cavernosum of a penis, the reservoir comprising a first major surface separated from to a second major surface by opposed side walls, wherein the first major surface and the second major surface both have a complex concave curvature with a lateral concave curvature between the opposed side walls and a longitudinal concave curvature between an end and a neck of the reservoir that are configured to form opposed depressions in the reservoir when the reservoir is empty of liquid.

17. The implantable penile prosthetic of claim 16, wherein the opposed side walls are connected between a first edge of the first major surface and a second edge of the second major surface, and a height of the opposed side walls is configured such that the first major surface is separated from the second major surface by less than one inch.

18. The implantable penile prosthetic of claim 16, wherein the opposed side walls are connected between a first edge of the first major surface and a second edge of the second major surface, with the first major surface concave relative to the first edge and the second major surface concave relative to the second edge.

19. The implantable penile prosthetic of claim 16, wherein a radius of curvature for the first major surface is less than a radius of curvature for the second major surface such that the reservoir has major surfaces with different concavity.

20. The implantable penile prosthetic of claim 19, wherein the first major surface is an outward facing surface and the second major surface is an inward facing surface when the reservoir is implanted, and the reservoir is configured to expand to contain liquid such that a majority of expansion for the reservoir is inward into the user to reduce perception of the implanted reservoir.

* * * * *